United States Patent
Corbeil

(10) Patent No.: US 12,029,588 B2
(45) Date of Patent: Jul. 9, 2024

(54) COOLING CHANNEL WITH NON-METALLIC HEAT SINK FOR A DIAGNOSTIC MEDICAL IMAGING APPARATUS

(71) Applicant: Siemens Medical Solutions USA, Inc., Malvern, PA (US)

(72) Inventor: James L. Corbeil, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 63 days.

(21) Appl. No.: 18/001,747

(22) PCT Filed: Aug. 26, 2020

(86) PCT No.: PCT/US2020/070462
§ 371 (c)(1),
(2) Date: Dec. 14, 2022

(87) PCT Pub. No.: WO2022/046153
PCT Pub. Date: Mar. 3, 2022

(65) Prior Publication Data
US 2023/0225679 A1    Jul. 20, 2023

(51) Int. Cl.
*A61B 5/00* (2006.01)
*A61B 5/055* (2006.01)
*G01R 33/34* (2006.01)
*G01R 33/385* (2006.01)

(52) U.S. Cl.
CPC .............. *A61B 5/704* (2013.01); *A61B 5/055* (2013.01); *G01R 33/3403* (2013.01); *G01R 33/3856* (2013.01)

(58) Field of Classification Search
CPC ......... A61B 5/704; A61B 5/055; A61B 6/037; A61B 6/4417; A61B 6/4488; A61B 6/032; G01R 33/3403; G01R 33/3856; G01R 33/481
See application file for complete search history.

(56) References Cited

U.S. PATENT DOCUMENTS

| | | | | |
|---|---|---|---|---|
| 8,590,331 | B2 * | 11/2013 | Corbeil | .................... G01T 1/16 62/259.1 |
| 2012/0091341 | A1 | 4/2012 | Corbeil et al. | |
| 2013/0284936 | A1 | 10/2013 | McBroom et al. | |
| 2017/0059720 | A1 | 3/2017 | McBroom et al. | |

OTHER PUBLICATIONS

International Search Report for Corresponding PCT Application No. PCT/US2020/070462, dated Jun. 1, 2021.

* cited by examiner

Primary Examiner — G. M. A Hyder

(57) ABSTRACT

A cooling channel in a gantry of a medical imaging apparatus transfers heat away from the radiation detector and detector electronics, while limiting influence on magnetic fields generated within the gantry, when incorporated in a magnetic resonance imaging (MRI) system. The cooling channel includes a non-electrically conducting, non-metallic housing in conductive thermal communication with the detector electronics and the radiation detector. A cooling conduit in the housing circulates coolant fluid. A unitary, non-electrically conductive, non-metallic heat sink in the housing is in direct conductive, thermal communication with the housing and the cooling conduit. A solid, thermally conductive layer is interposed between and affixed to opposing, spaced exterior surfaces of the conduit and the heat sink.

20 Claims, 5 Drawing Sheets

COOLING CHANNEL WITH NON-METALLIC HEAT SINK FOR A DIAGNOSTIC MEDICAL IMAGING APPARATUS

TECHNICAL FIELD

A cooling system for a gantry of a diagnostic medical imaging apparatus. More particularly, the gantry cooling system incorporates a cooling channel for radiation detectors and detector electronics, with a non-metallic heat sink coupled to a fluid-cooled cooling conduit by a solid, thermally conductive layer.

BACKGROUND

Diagnostic medical imaging apparatuses include, by way of non-limiting example, computed tomography (CT), two-dimensional digital radiography (DR), magnetic resonance imaging (MRI), positron emission tomography (PET), single photon emission computed tomography (SPECT) modalities. Hybrid modality apparatuses include, by way of non-limiting example, PET/CT, PET/MRI, SPECT/CT and SPECT/MRI, which combine in a single system the local imaging resolution benefits of CT or MRI and the sensitivity for imaging and detecting cellular and metabolic biological processes in a patient. Many of these imaging apparatuses or systems include a toroidal-shaped gantry structure through which is inserted a patient table. The gantry includes one or more electromagnetic radiation detectors, which emit electrons in response to incident photons of electromagnetic radiation. In some modalities, the incident photons are transmitted X-rays or ionized radiation emissions at the higher end of the electromagnetic frequency range (e.g., CT, DR, PET, SPECT), while in other modalities (e.g., MRI) the incident photons are within the radio frequency range. The output electrons of the detector are processed by detector electronics to generate detector output signals, which are subsequently processed by the imaging apparatus to generate or construct patient images. In some imaging systems, detector electronics packages are housed with the detectors within the gantry structure in an integrated detector assembly.

Exemplary electromagnetic radiation detectors include photomultiplier tubes (PMTs) and solid-state detectors, such as avalanche photo diodes (APDs) and silicon photomultipliers (SiPMs). Signal gain of solid-state detectors are more temperature dependent than PMTs. The solid-state photon sensors and their detector electronics packages are typically maintained within relatively narrow temperature fluctuation and operational temperature bandwidths to reduce the likelihood of inaccurate detector readings and/or excessive noise generation components in the detector readings that otherwise might lead to poor quality patient images. The solid-state radiation detectors require external cooling to maintain detector assemblies within defined temperature fluctuation and bandwidth specifications. Typically, radiation detectors in medical imaging systems are cooled by blowing cooling air over them, or by transferring detector heat to one or more conduits that circulate cooling fluid in proximity to them.

SUMMARY

A cooling channel in a gantry of a medical imaging apparatus transfers heat away from the radiation detector and detector electronics. When the cooling channel is incorporated within the scanning field of a MR gradient tube of an MRI system's gantry, it may produce eddy currents by the electro-magnetic fields generated within the gantry. Eddy currents contribute to MR image distortion, such as artifact ghosting. Embodiments of the cooling channels include a non-electrically conducting, non-metallic housing in conductive thermal communication with the detector electronics and the radiation detector. A cooling conduit in the housing circulates coolant fluid. A unitary, non-electrically conductive, non-metallic heat sink in the housing is in direct conductive, thermal communication with the housing and the cooling conduit. A solid, thermally conductive layer is interposed between and affixed to opposing, spaced exterior surfaces of the conduit and the heat sink.

Exemplary embodiments described herein transfer imaging apparatus generated heat, including gantry heat, to fluid-cooled, cooling channels. The cooling channel construction reduces the effects of magnetic and gradient fields, as well as ohmic and eddy current heating that are induced in the gantry during patient scans, all of which otherwise would degrade patient image quality. In some embodiments, the cooling channel is incorporated in a non-metallic housing interposed between the radiation detector and the detector electronics in a radiation detector assembly. The housing has a planar lower surface for coupling to the radiation detector and a planar upper surface for coupling to the detector electronics. The cooling channel includes a cooling conduit, for circulation of a fluid coolant, via an inlet and an outlet. Heat generated within the detector assembly is transferred to the coolant. In recirculating coolant systems, the coolant in turn transfers its retained heat to a gantry cooling system located in the gantry, or in another portion of the medical imaging system, or to a remotely located cooling system. In some embodiments, the cooling channel incorporates a unitary, non-metallic heat sink that draws heat from the detector and, in many embodiments, the detector electronics. The heat sink has respective continuous top and bottom surfaces in direct heat-conductive communication with the respective upper and lower surfaces of the housing, and a lateral surface between the top and bottom surfaces. The lateral surface is in opposed, spaced orientation with an exterior surface of the conduit. The respective exterior surface profiles of the lateral surface of the heat sink and the conduit conform to each other and are affixed to each other with a solid, thermally conductive layer.

The cooling channel construction transfers heat by direct thermal conduction from the radiation detector and/or detector electronics to the upper and lower surfaces of the housing. The housing in turn directly transfers heat by thermal conduction to the heat sink. In some embodiments, the housing also directly transfers heat by thermal conduction to the conduit. The heat sink directly transfers heat by thermal conduction to the affixed solid, thermally conductive layer; the conductive layer in turn directly transfers heat by thermal conduction to the conduit. Thus, in some embodiments, through a series of conductive heat transfer interfaces of the cooling channel, heat is transferred from the radiation detector and detector electronics to the circulating coolant by efficient, conductive heat transfer.

In some embodiments, the housing, cooling conduit and the heat sink are non-metallic and non-electrically conductive. In those exemplary embodiments the housing and the conduit are constructed from hardened resin or polymer materials, and heat sink is constructed from ceramic material. In those embodiments, the thermally conductive layer that affixes the heat sink to the conduit is a thermally conductive adhesive. In some embodiments, the thermally conductive adhesive incorporates electrically conductive (e.g., metallic) constituents to enhance conductive heat transfer from the heat sink to the conduit. Totally non-metallic, non-electrically conductive cooling channel construction greatly reduces the effects of magnetic and gradient fields, as well as ohmic and eddy current heating that are induced in the gantry during patient scans, which otherwise would degrade patient image quality.

In other cooling channel embodiments, such as in applications where a higher heat transfer rate is required than is achievable with low- or non-metallic construction, the housing is constructed from hardened resin or polymer materials, the heat sink is constructed from ceramic material, and the conduit is constructed from metal, such as metal tubing. In these embodiments, the thermally conductive layer that affixes the outer profile of the metal conduit to the ceramic heat sink is a metal solder bonded to the conduit and to a metallic layer that was deposited on the lateral surface of the heat sink. The deposited metallic layer on the ceramic heat sink bonds to the solder. Thus, the metallic, highly thermally conductive layer, efficiently transfers heat from the ceramic heat sink to the metal conduit. In some embodiments, the housing is also in direct contact with the metal cooling conduit, for direct conductive heat transfer between those components.

In other exemplary embodiments of the cooling channel, the cooling conduit has a u-shaped planar profile, with first and second opposed branches joined at proximal ends. Those branches respectively define first and second exterior surface profiles that are inwardly facing relative to each other. An inlet is oriented on a distal end of the first branch, while an outlet is oriented on a distal end of the second branch. The heat sink is oriented between the first and second branches, with first and second opposed lateral surfaces. Each of the respective first and second lateral surfaces defines respective first and second exterior surface profiles conforming respectively to the corresponding inwardly facing, exterior profiles of the first and second branches. The corresponding lateral surfaces of the heat sink and the inwardly facing exterior surface profiles of the branches are in opposed, spaced orientation relative to each other. The respective top and bottom surfaces of the heat sink each has a surface area of sixty to eighty-five (60%-85%) percent of the corresponding surface area of its corresponding, respective upper and lower surface of the housing. First and second solid, thermally conductive layers are respectively interposed between and affixed to each of the respective corresponding, first, and second exterior surface profiles of the heat sink, and those of the first and second branches.

Other embodiments feature a medical imaging apparatus, such as a PET/MRI system, having a gantry, a coolant loop in the gantry, for absorption of heat generated within the gantry and a gantry cooling apparatus coupled to the coolant loop, for receiving heat generated within the gantry. Coolant fluid circulates within the coolant loop. The gantry also includes a magnetic resonance imaging tube. The imaging tube includes therein at least one electromagnetic radiation detector, a detector electronics package coupled to the radiation detector, for receiving signals generated by the radiation detector. The imaging tube includes therein a cooling channel having a non-metallic housing. The housing has a planar lower surface, coupled to electromagnetic radiation detector, and a planar upper surface coupled to the detector electronics package. A cooling conduit in the housing has an exterior surface profile, an inlet and an outlet respectively coupled to the coolant loop for circulation of the coolant fluid therethrough. A unitary, non-metallic heat sink is in the housing. The heat sink has respective continuous top and bottom surfaces in direct heat-conductive communication with the respective upper and lower surfaces of the housing, and a lateral surface between the top and bottom surfaces. The lateral surface has an exterior surface profile conforming to the exterior surface profile of the conduit, which is in opposed, spaced orientation with the conduit. A solid, thermally conductive layer is interposed between and affixed to the respective opposed, exterior surface profiles of the conduit and the heat sink.

Additional exemplary embodiments feature methods for making cooling channel for a gantry of a diagnostic medical imaging apparatus. In an exemplary method, the cooling conduit is fabricated with an inlet, an outlet, and an exterior surface having a surface profile. A unitary, non-metallic heat sink is fabricated, with respective continuous top and bottom surfaces, and a lateral surface between the top and bottom surfaces, having an exterior surface profile conforming to the exterior surface profile of the conduit. The exterior surface profile of the conduit and the corresponding portion of the exterior surface profile of the heat sink are placed in opposed, spaced orientation and then rigidly coupled to each other by interposing and affixing a solid, thermally conductive layer to their respective corresponding, opposed and spaced exterior surfaces. The now coupled conduit and heat sink are enveloped within a non-metallic housing, having respective planar upper and lower surfaces in direct heat-conductive communication with the respective top and bottom surfaces of the heat sink. The inlet and an outlet of the conduit accessible outside the housing.

In some of the method embodiments, the heat sink is fabricated as a monolithic block of ceramic material and the cooling conduit is constructed from metal, such as metal tubing. In embodiments incorporating a metal conduit and a ceramic heat sink, they are rigidly coupled by depositing a metallic layer on the portion of the exterior surface of the ceramic heatsink that is coupled to the corresponding exterior surface profile of the conduit and soldering the metallic layer previously deposited on the ceramic heatsink to the corresponding exterior surface profile of the conduit. In some embodiments, the coupled conduit and heat sink are enveloped by placing them in a mold and encapsulating them by filling the mold with non-solid, non-metallic material, such as polyurethane liquid, and hardening the non-metallic material to form a rigid housing.

In other method embodiments, a metallic cooling conduit is fabricated with a u-shaped planar profile, having first and second opposed branches joined at proximal ends. The branches respectively define first and second exterior surface profiles that are inwardly facing and laterally spaced relative to each other. The inlet is oriented on a distal end of the first branch and the outlet is oriented on the distal end of the second branch. A ceramic heat sink is fabricated with first and second opposed lateral surfaces, with each of the respective first and second lateral surfaces defining respective first and second exterior surface profiles conforming respectively to the corresponding inwardly facing, exterior profiles of the first and second branches. The heat sink is inserted between the first and second branches, so that its respective first and second exterior surface profiles are in opposed, spaced orientation with the respective corresponding, inwardly facing, exterior profiles of the first and second branches. The first and second branches of the conduit are coupled to each of their corresponding first and second exterior surface profiles of the heat sink, by depositing respective metallic layers and soldering them to the corresponding exterior profiles of the first and second branches.

The respective features of the exemplary embodiments that are described herein may be applied jointly or severally in any combination or sub-combination.

BRIEF DESCRIPTION OF DRAWINGS

The exemplary embodiments are further described in the following detailed description in conjunction with the accompanying drawings, in which.

To facilitate understanding, identical reference numerals have been used, where possible, to designate identical elements that are common to the figures. The figures are not drawn to scale.

DESCRIPTION OF EMBODIMENTS

Figure 1:
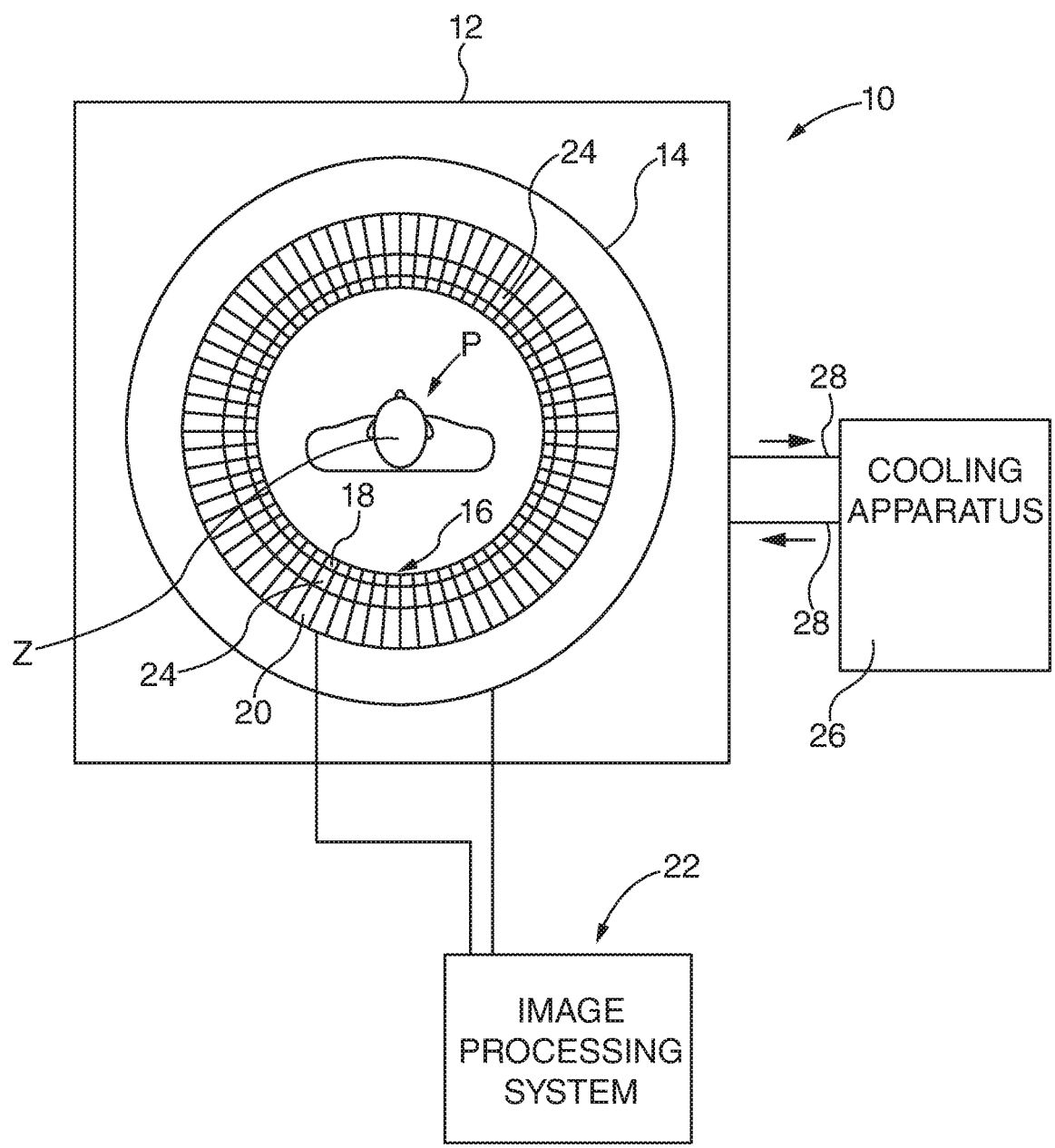
FIG. 1 is a front elevational view of a gantry of a combination PET/MRI medical imaging scanner for generating PET and/or MRI images of a patient, which incorporates detector assemblies, respectively including a radiation detector, detector electronics, and a cooling channel.

Medical imaging apparatus with cooling systems incorporating cooling channel embodiments described herein, in one or more of their detector packages, transfer heat out of system's gantry to maintain radiation detector and detector electronics within a designated temperature range, reducing the likelihood of temperature-related degradation of patient images. Various embodiments of these cooling channels are suitable for computed tomography (CT), two-dimensional digital radiography (DR), positron emission tomography (PET), and single photon emission computed tomography (SPECT) modalities. Various embodiments of the cooling channels are also suitable for hybrid modality apparatuses that incorporate magnetic resonance imaging (MRI) and another modality, (e.g., PET/MRI or SPECT/MRI) where one or more cooling channels are oriented within the MRI tube scanning field. Efficient cooling attributes of embodiments of these cooling channels are useful for detector assemblies that incorporate solid-state avalanche photo diodes (APDs) and silicon photomultipliers (SIPMs). as these types of solid-state detectors are typically more susceptible to higher temperatures than photo multiplier tubes (PMTs). These cooling channel embodiments achieve high heat-load transfer out of the gantry of the imaging apparatus, while reducing: magnetic field distortions within the MR scanning field, ohmic heating, and eddy current heating, when incorporated in gantries of combination PET/MRI and SPECT/MRI imaging systems.

In the case of an MRI system, locating an array of radiation imaging detectors inside the patient imaging bore of its gantry, as is done in the imaging tube of combination PET/MRI and SPECT/MRI imaging systems, presents technical challenges. The challenges include, by way of non-limiting example, spatial constraints, distortions in magnetic and gradient fields generated during an MRI scan of a patient, as well as ohmic and eddy current heating. In general, the magnetic field strength and spatial constraints of a combination PET/MRI or SPECT/MRI system generally limit radiation detector sensor selection to solid-state types, such as avalanche photo diodes (APDs) and silicon photo multipliers (SiPMs). Solid-state photon sensors, such as APDs and SiPMs, are relatively small in height (1-2 mm) and are typically unaffected by the magnetic fields of an MRI system, as compared to larger PMTs and the materials of their components, but their gain is more susceptible to fluctuations in temperature. PMTs are evacuated tubes and do not respond to temperature changes as fast as APDs and SiPMs.

As noted, the cooling channel embodiments herein are capable of transferring heat away from APD- and SiPM-type detectors. They incorporate non-metallic, non-electrically conductive materials that reduce the likelihood of gantry heating attributable to eddy current heating, ohmic heating and frictional heating when the detector assembly is in the electro-magnetic field generated MRI imaging tube, such as by a PET/MRI system. The non-metallic, non-electrically conductive materials in the cooling channel embodiments are also relatively more transparent to the electro-magnetic field generated within the MRI imaging tube, which reduces MR image artifacts, including by way of non-limiting example, artifact ghosting when using the MR system to perform echo planar imaging (EPI), rapid-imaging scans. Thus, the cooling channel embodiments maintain solid-state detectors within required temperature parameters to reduce temperature-gain distortions to patient PET and SPECT images, while being relatively transparent within MR fields, to reduce artifact ghosting and other distortions to MR images.

Embodiments of the cooling channel efficiently transfer heat from the detector assembly of any modality of medical imaging apparatus by enhancing direct conductive heat transfer from radiation detectors and detector electronics to coolant in the cooling system. The cooling channel can maintain solid-state detectors and the detector electronics within temperature range bandwidths during scanner operation, despite their incorporation of non-electrically conductive, non-metallic components that generally have lower thermal conductivity than metal components. In combination MRI/PET or MRI/SPECT scanners, lower metal content reduces eddy current and ohmic heating, and Lorenz forces (vibrational) of the cooling channel, induced in the electro-magnetic field of the MRI tube, which would otherwise raise ambient temperature in the detector assembly, cause a spiking artifact, or damage the detector. Lower metal content in the cooling channel embodiments also reduces eddy current-induced artifacts in the MR image. Lowering electro-magnetically conductive material content in the detector assemblies beneficially lowers ambient temperature in the gantry and beneficially reduces disruptions of the MR scanning field in the MR imaging tube. The presently disclosed gantry cooling system embodiments can transfer sufficient heat out of the gantry to maintain ambient operational temperature bandwidth and fluctuation specifications of the imaging system, despite use of non-metallic components within the cooling channels.

FIG. 1, shows a PET/MRI imaging apparatus or system 10 for generating an overlaid MRI and PET image display. The apparatus 10 includes a gantry 12. A MRI gradient tube 14 in the gantry 12 defines a longitudinal direction axis Z, extending orthogonally in relation to the plane of the drawing of FIG. 1. A plurality of PET detector assemblies 16 (hereafter, detector assemblies) are arranged coaxially within the MRI tubes 14 in opposing pairs radially spaced from the longitudinal direction axis Z. Each detector assembly 16 includes a radiation detector 18, facing the patient P. Exemplary radiation detectors include avalanche photo diodes (APDs) or silicon photomultipliers (SiPMs). A detector electronics package 20 (hereafter, detector electronics) receives signals from the radiation detector 18 that are indicative of photons sensed by an array of detector crystals in the detector, via a signal pathway, such as a plug-in terminal-type, electrical connector 21. Each detector electronics 20 generates respective detector output signals that are subsequently processed by an image processing unit 22 to generate or construct patient images. The plurality of detector assemblies 16 define along the longitudinal direction Z a cylindrical, PET image field, with images generated by the image processing unit 22. Along its coaxial, longitudinal direction Z the MRI tube 14 defines a cylindrical, MR image field, with images also generated by the image processing unit 22. This is implemented by a corresponding adaptation of the arrangement density of the PET detector assemblies 16 along the longitudinal direction Z to provide simultaneous imaging in both modalities. In operation, the PET and RM image fields essentially match each other and both image scans are performed in tandem.

Each detector assembly 16 incorporates a cooling channel 24, for transferring heat generated within the detector assembly to a gantry cooling system 26, by circulation of fluid coolant in a cooling loop 28. In recirculating coolant systems, the coolant in turn transfers its retained heat to the gantry cooling system, which is typically located in the gantry, or in another portion of the medical imaging system, or to a remotely located cooling system as shown in FIG. 1. In some modality embodiments incorporating MR scan capability, coolant fed within the cooling loop 28 is first routed to the detector assemblies 16, and then the return coolant is routed through gradient coils of the MR system before returning to a chiller of the cooling system 26.

In the embodiment of FIGS. 1-4, the cooling channel 24 is interposed between each radiation detector 18 and its detector electronics 20. The cooling channel 24 comprises a non-metallic housing 30, with a planar lower surface 32, for abutting coupling to a corresponding planar surface of the radiation detector 18 and a planar upper surface 34, for abutting coupling to a corresponding planar surface of the detector electronics 20. Fasteners (not shown) couple the radiation detector 18 and the detector electronics 20 to the housing 30. In other embodiments, the respective abutting surfaces of the detector 18, the detector electronics 20 and the housing define other mutually confirming shapes. In some embodiments, the plug-in terminal-type, electrical connector 21 is oriented in a through-channel of the housing 30. The cooling channel 24 includes a cooling conduit 36 in the housing 30, for circulation of the fluid coolant within the cooling loop 28 of the gantry cooling system 26, via an inlet 38 and an outlet 40. The cooling conduit 36 is a metal tube, but in other embodiments the conduit is constructed of non-metallic materials, such as polymer. Generally, metallic cooling conduits are utilized to achieve higher heat transfer rate to the coolant in the cooling loop 28 than is possible with a non-metallic conduit, so long as the metal structure does not cause unacceptable distortion of patient images, especially MR images in combination MRI/PET or MRI/SPECT systems.

The cooling conduit 36 has a u-shaped planar profile, with opposed first 42 and second 44 branches joined at proximal ends. A distal end of the first branch 42 incorporates the inlet 38, while the distal end of the second branch 44 incorporates the outlet 40. The cooling conduit 36 has a flattened oval cross section, with flattened lower 46 and upper 48 surfaces, respectively in direct heat-conductive contact with the lower 32 and upper 34 planar surfaces of the housing 30. The opposed first 42 and second 44 branches respectively define inwardly facing first 50 and second 52 exterior surface profiles that are inwardly facing relative to each other.

The cooling channel 24 includes a non-metallic, non-electrically conductive heat sink 54 within the housing, with respective continuous top 56 and bottom 58 surfaces in direct heat-conductive communication with the respective upper 34 and lower 32 surfaces of the housing 30. In some embodiments, the respective top 56 and bottom 58 surfaces of the heat sink 54 each has a surface area of sixty to eighty five percent (60%-85%) of the corresponding surface area of its corresponding, respective upper 34 and lower 32 surfaces of the housing 30. In some embodiments the heat sink 54 is formed from a monolithic block of ceramic material or formed by casting and curing ceramic slurry. In other embodiments, the heat sink 54 is a unistructural fabrication of affixed ceramic subcomponents. Various embodiments of the heat sink 54 are constructed from one or more of the following ceramic materials: Silicon Nitride, Boron Carbide, Aluminum Nitride, Alumina, and Silicon Carbide.

The heat sink 54 is oriented between the first 42 and second 44 branches of the conduit 36, with first 60 and second 62 opposed lateral surfaces. The exterior surface profile of each of the respective first 60 and second 62 lateral surfaces conform to the respective first 50 and second 52 inwardly facing, exterior surface profiles of the first 42 and second 44 branches of the conduit 36. The respective pairs of surfaces, 50 and 42, 52 and 44 are in opposed, spaced orientation relative to each other.

A first solid, thermally conductive layer 64 is interposed between and affixed to each of the respective corresponding, first 60 and first 50 exterior surface profiles of the lateral surface of the heat sink 54 and that of the first branch 42 of the conduit 36. Similarly, a second thermally conductive layer 66 is interposed between and affixed to each of the respective corresponding, second 62 and second 52 exterior surface profiles of the lateral surface of the heat sink 54 and that of the second branch 44 of the conduit 36. The solid, thermally conductive layer, adhering directly to the opposing surfaces of the heat sink 54 and the conduit 36 has a higher overall thermal conductivity than a contactless gap, or mere surface contact, or application of non-solid thermally conductive grease between those components. The solid, thermally conductive layers 64 and 66 facilitate direct, thermally conductive heat transfer from the lateral surfaces of the heat sink 54 to the cooling conduit 36.

Solid affixation of the conduit 36 and the heat sink 54 to each other enhances overall structural integrity of the cooling channel 24 and inhibits relative shifting of the metallic cooling conduit 36, caused by induced Lorenz forces when the cooling channel exposed to an electro-magnetic field within the MR tube 14. By avoiding relative shifting of the metallic conduit 36, generate noise in the electro-magnetic field generated in the MR tube 14 or damage the PET detector. The former is beneficial to maintaining the integrity of the radiation detectors 18, to avoid CT, PET or SPECT image distortion. The latter is beneficial to reduce likelihood of image artifacts, spiking, in a MR image.

Each of the first 64 and second 66 conductive layers comprises a metallic layer 68 deposited on its corresponding exterior lateral surface 60 or 62 of the non-metallic heat sink 54. It is preferable that the deposit area of the metallic layer 68 be limited to the zones of the lateral surfaces 60 and 62 that oppose their corresponding exterior surfaces 50 and 52 of the conduit, in order to minimize total metal content within the cooling channel 24. A solder layer 70 is affixed to its corresponding metallic layer 68 and to its corresponding exterior surface profile 50 or 52 of its corresponding conduit branch 42 or 44, completing affixation of those components to each other. The hardened, solid solder layer 70 is relatively soft and flexible, which beneficially accommodates different thermal expansion rates of the different materials in the cooling conduit 36 and the heat sink 54. Thermal conductivity range of commercially available solders is approximately 50-80 W/m-K.

In other cooling channel embodiments, the conductive layer 64 and/or 66 comprises a solid, thermally conductive adhesive, having a higher thermal conductivity than non-thermally conductive adhesives. The thermally conductive adhesive adheres to and rigidly affixes the cooling conduit 36 and the heat sink 54 to each other. Thermally conductive adhesive is used to bond non-metallic cooling conduits and heat sinks to each other, when it is not feasible to affix them with a deposited metallic coating and solder, e.g., when the cooling conduit is constructed with a polymer material. Thermal conductivity of commercially available thermally conductive adhesive is approximately 1 W/m-K.

Figure 2:
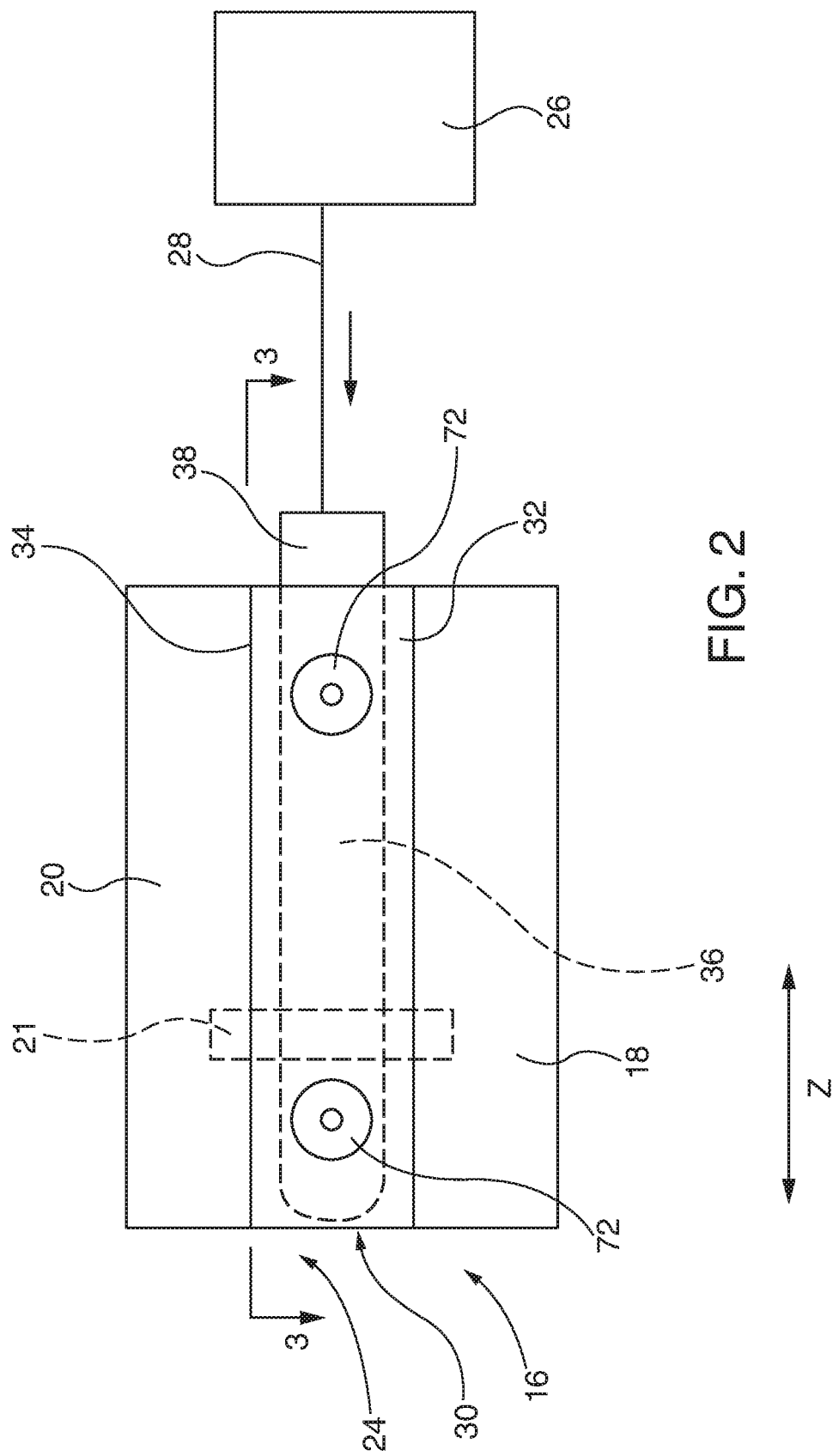
FIG. 2 is a side elevational view of the detector assembly of the PET/MRI scanner of FIG. 1.
Figure 3:
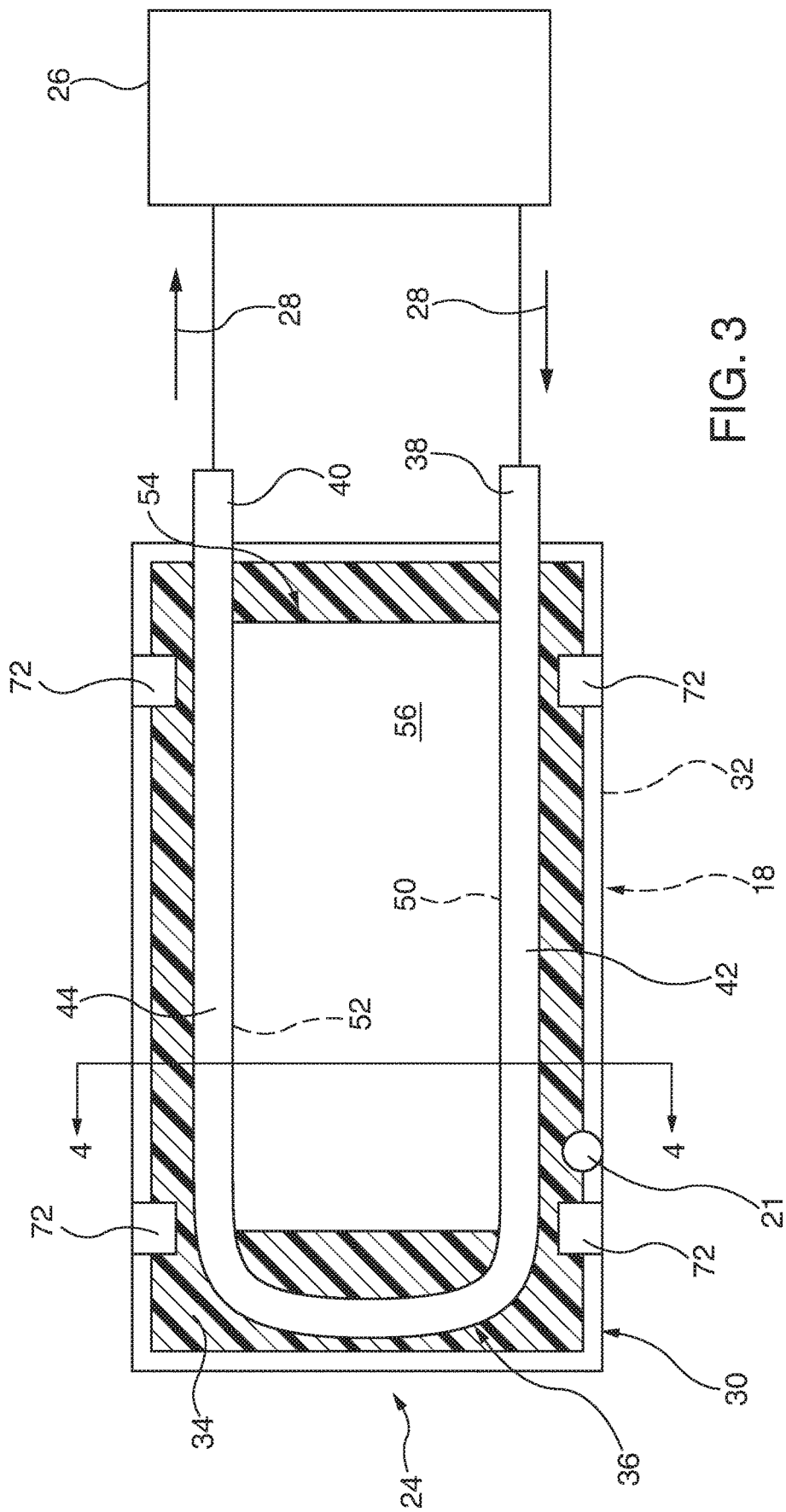
FIG. 3 is a cross-sectional plan view of the cooling channel of the detector assembly of FIG. 2.
Figure 4:
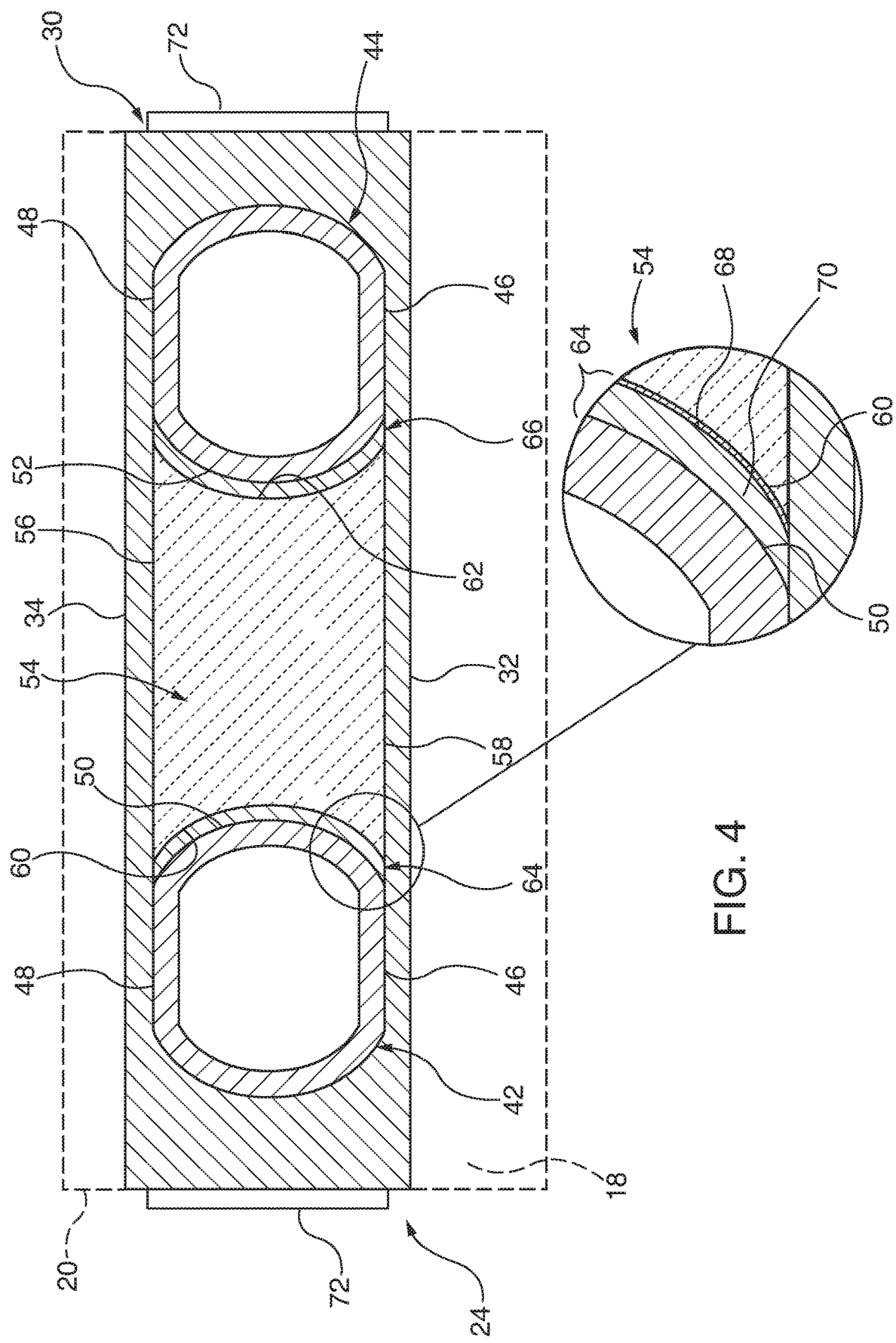
FIG. 4 is an elevational cross section of the cooling channel of FIG. 3.

In the embodiment of the cooling channel 24 of FIGS. 2-4, female threaded fasteners 72 are embedded in or otherwise affixed to lateral sides of the housing 30, between its lower 32 and upper 34 surfaces, for selective direct or indirect coupling of the cooling channel to the gantry 12. In some embodiments, the fasteners 72 are constructed of non-metallic, non-electrically conductive material, to minimize metal content of the detector assembly 16.

In the embodiment of the cooling channel 24 of FIGS. 1-4, heat generated in the detector assembly 16, by the radiation detector 18 and the detector electronics 20 is ultimately transferred coolant circulating in the coolant loop 28 in a sequence of direct conductive thermal junctures through the cooling channel 24. Specifically, the cooling conduit 36 and the heat sink 54 are embedded in and in direct thermally conductive contact with the material forming the housing 30. Heat generated in the detector assembly 16, by the radiation detector 18 and the detector electronics 20 is initially transferred to the cooling channel 24, through corresponding lower 32 and upper 34 surfaces of the housing 30. The upper 34 and lower 32 surfaces of the housing 30 are in turn in direct contact and in conductive thermal communication with their respective corresponding upper 48 and lower 46 surfaces of the cooling conduit 36. Heat so absorbed by the conduit 36 is transferred in turn to the circulating coolant in the coolant loop 28. Similarly, the upper 34 and lower 32 surfaces of the housing 30 are in direct contact and in conductive thermal communication with their respective corresponding top 56 and bottom 58 surfaces of the heat sink 54. Heat absorbed by the top 56 and bottom 58 surfaces of the heat sink 54 is in turn transferred by conductive thermal communication to the cooling conduit 36, through their first 60 and second 62 lateral surfaces and the respective first 64 and second 66 conductive layers.

FIGS. 5-8 are alternative embodiments of cooling channels, which incorporate different flow paths of their cooling conduits and different placements of heat sinks. Each of the embodiments of FIGS. 5-8 share similarities with the embodiment of the cooling channel 24 of FIGS. 1-4 described in the immediately previous paragraph. Heat generated by the radiation detector and the detector electronics is ultimately transferred coolant circulating in the coolant loop in a sequence of direct conductive thermal junctures through each of the alternative cooling channel embodiments.

Figure 5:
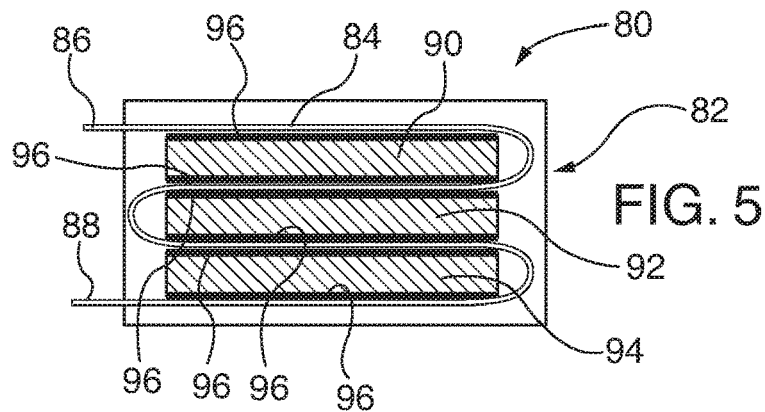
FIGS. 5-8 are elevational cross sections, of alternative embodiment cooling channels.

In the embodiment of FIG. 5, the cooling channel 80 has a housing 82, in which is embedded a triple loop, serpentine cooling conduit 84, with an inlet 86 and an outlet 88 for circulation of coolant. A trio of heat sinks 90, 92 and 94 are interposed between serpentine coils of the conduit 84. Thermally conductive layers 96 affix opposed, corresponding exterior surfaces of the conduit 84 and the heat sinks 90, 92 and 94.

Figure 6:
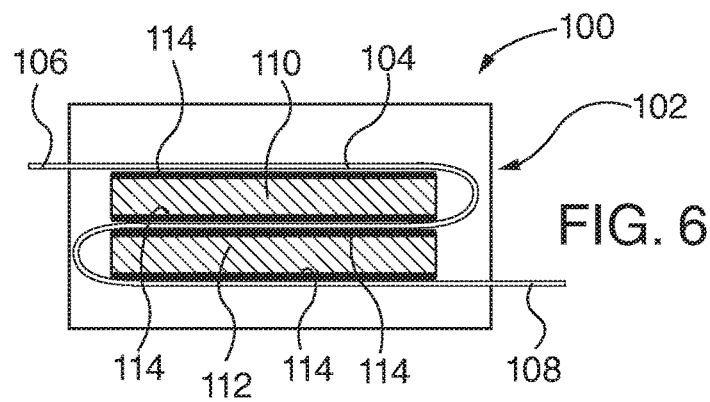

In the embodiment of FIG. 6, the cooling channel 100 has a housing 102, in which is embedded a double loop, serpentine cooling conduit 104, with an inlet 106 and an outlet 108 for circulation of coolant. A pair of heat sinks 110 and 112 are interposed between serpentine coils of the conduit 104. Thermally conductive layers 114 affix opposed, corresponding exterior surfaces of the conduit 104 and the heat sinks 110 and 112.

Figure 7:
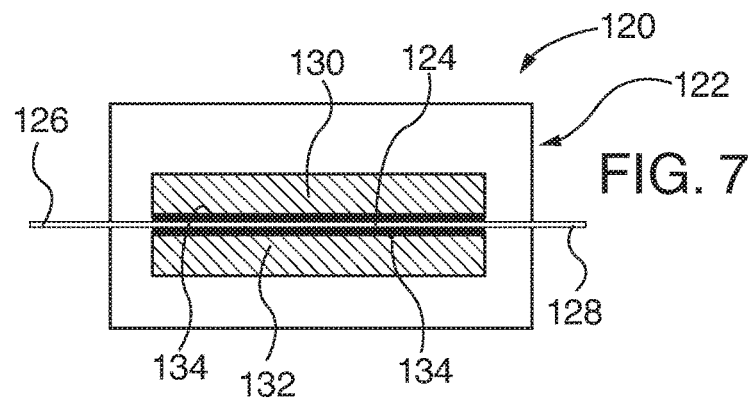

In the embodiment of FIG. 7, the cooling channel 120 has a housing 122, in which is embedded a single loop cooling conduit 124, with an inlet 126 and an outlet 128 for circulation of coolant. A pair of heat sinks 130 and 132 flank the conduit 124. Thermally conductive layers 134 affix opposed, corresponding exterior surfaces of the conduit 124 and the heat sinks 130 and 132.

Figure 8:
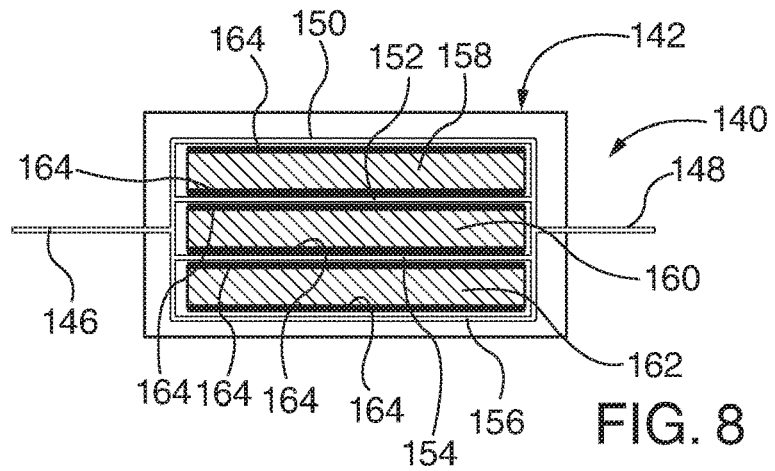

In the embodiment of FIG. 8, the cooling channel 140 has a housing 142, in which is embedded a multi-tube, parallel flow cooling conduit 144, with an inlet 146 and an outlet 148 for circulation of coolant. In this embodiment, the cooling conduit 144 has four parallel branch conduits 150, 152, 154 and 156. A trio of heat sinks 158, 160 and 162 are interposed between opposing pairs of the branch conduits. Thermally conductive layers 164 affix opposed, corresponding exterior surfaces of the branch conduits 150, 152, 154 and the corresponding heat sinks 158, 160 and 162.

An exemplary method for making any of the cooling channels 24, 80, 100, 120 and 140 is now described. For brevity, this description focuses on the method for making the cooling channel 24. The cooling conduit 36 and the heat sink 54 are fabricated. In some embodiments, the cooling conduit 36 is fabricated by shaping metal tubing having the planar and cross-sectional profiles shown in FIGS. 3 and 4. Similarly, the heat sink 54 is fabricated with the first 60 and second 62 lateral edges matching the respective profiles of their corresponding first 50 and second 52 exterior surface profiles of the cooling conduit first 42 and second 44 branches.

The first 60 and second 62 lateral edges of the heat sink 54 are metalized by depositing the metallic layer 68 on them. In some embodiments, the metallic layer is deposited on the lateral surfaces 60 and/or 62, by painting them with metallic paint (e.g., palladium or platinum paint), that facilitates electroplating, or the metal may be deposited by electron-beam deposition, sputter coating, or by vapor deposition. Then, first 42 and second 44 branches of the cooling conduit 36 are advanced over the corresponding first 60 and second 62, now metalized lateral edges of the heat sink 54. Thereafter, the respective first 64 and second 66 conductive layers are completed by soldering together the respective metalized lateral edges 60 and 62 of the heat sink 54 and their corresponding first 50 and second 52 exterior surface profiles of the cooling conduit, creating a solidified solder joint 70 with a relatively high thermal conductivity. In other embodiments, the lateral edges 60 and 62 of the heat sink are not metalized and the first 64 and second 66 conductive layers comprise thermally conducted adhesive that once cured, bonds or otherwise affixes the cooling conduit 36 and the heat sink 54 to each other. Thermally conductive adhesive is utilized to create the conductive layers 64 and/or 66 in cooling channel embodiments that utilize non-metallic cooling conduits.

Whether the conductive layers 64 or 66 are formed with a metallic layer and solder or an adhesive layer, the now affixed cooling conduit 36 and the heat sink 54 are enveloped or otherwise encapsulated in a non-metallic housing 30, along with any desired fasteners 72. The inlet 38 and the outlet 40 of the cooling conduit, and engagement surfaces of any fasteners 72 remain exposed outside the housing 30. In some embodiments, the housing is formed by placing the affixed cooling conduit 36 and the heat sink 54 components and any fasteners 72 in a mold (not shown). The mold is filled with non-solid, non-metallic material, such as polyurethane, or other thermoplastic or thermosetting resins. Thereafter that material is hardened to form the now rigid housing 30. All the cooling conduit 36 and the heat sink 54 components encapsulated within the housing 30 are now rigidly positioned, and they are in direct conductive thermal communication with each other. In some embodiments the mold is removed after the housing material is cured and hardened. In other embodiments, the mold remains in place as an exterior shell of the housing 30.

The completed cooling channel 24 is ready for incorporation into a detector assembly 16 by forming a through passage in the housing 30 between its respective upper 34 and lower 32 surfaces for receipt of the electrical connector 21, such as a plug-in terminal block. In some embodiments, the through passage is formed in the mold before pouring of the filler material, by placement of a mold insert that is removed after the filler material is at least partially hardened. In other embodiments, the through passage is formed after filler material hardening, by removing the hardened material with a drill or other cutting tool. The terminal block or other electrical connector 21 is then inserted in the through passage of the housing 30. The electromagnetic radiation detector 18 is coupled to the electrical connector 21 and solidly coupled, with fasteners, in abutting contact with the lower surface 32 of the housing 30, for direct, conductive thermal communication therebetween. Similarly, the detector electronics package 20 is coupled to the electrical connector 21 so that it can receive signals generated by the radiation detector 18 through the signal pathway established by the electrical connector. The detector electronics package 20 is solidly coupled, with fasteners, in abutting contact with the upper surface 34 of the housing 30, for direct, conductive thermal communication therebetween. The completed detector assembly 16 is now ready for installation into a gantry 12 of a medical imaging apparatus 10.

Although various embodiments have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the phraseology and terminology used herein is for the purpose of description and should not be regarded as limiting. The use of "including", "comprising", or "having", and variations thereof herein is meant to encompass the items listed thereafter and equivalents thereof as well as additional items. Unless specified or limited otherwise, the terms "mounted", "connected", "supported", and "coupled" and variations thereof are to be interpreted broadly; they encompass direct and indirect mountings, connections, supports, and couplings.

What is claimed is:

1. A cooling channel for a gantry of a diagnostic medical imaging apparatus, comprising:
    a non-metallic housing having a lower surface, for abutting contact and coupling to an electromagnetic radiation detector, and an upper surface for abutting contact and coupling to a detector electronics package;
    a cooling conduit in the housing, for circulation of coolant fluid therethrough, the conduit having an inlet and an outlet respectively accessible outside the housing, and an exterior surface profile;
    a unitary, non-metallic heat sink in the housing, having:
    respective continuous top and bottom surfaces in direct heat-conductive communication with the respective upper and lower surfaces of the housing, and
    a lateral surface between the top and bottom surfaces, having an exterior surface profile conforming to the exterior surface profile of the conduit, in opposed, spaced orientation with the conduit; and
    a solid, thermally conductive layer interposed between and affixed to the respective opposed, exterior surface profiles of the conduit and the heat sink.

2. The cooling channel of claim 1, the heat sink comprising a monolithic block of ceramic material.

3. The cooling channel of claim 2, further comprising:
    the conduit constructed of metal; and
    the conductive layer having a metallic layer deposited on the exterior surface profile of the heat sink; and a solder layer affixed to the metallic layer and to the exterior surface profile of the conduit.

4. The cooling channel of claim 1, the conductive layer comprising thermally conductive adhesive.

5. The cooling channel of claim 1, further comprising:
    the conduit constructed of metal; and
    the conductive layer having a metallic layer deposited on the exterior surface profile of the heat sink; and a solder layer affixed to the metallic layer and to the exterior surface profile of the conduit.

6. The cooling channel of claim 1, the inlet and outlet oriented on opposite ends of the housing.

7. The cooling channel of claim 6, further comprising the cooling conduit having a serpentine-shaped planar profile.

8. The cooling channel of claim 1, incorporated within a detector assembly, further comprising:
    an electromagnetic radiation detector coupled to the lower surface of the housing;
    a detector electronics package coupled to the upper surface of the housing; and
    an electrical connector, passing through the upper and lower planar surfaces of the housing for communicating signals generated by the radiation detector to the detector electronics package.

9. The cooling channel of claim 1, further comprising:
    the cooling conduit having a u-shaped planar profile, with first and second opposed branches joined at proximal ends thereof that respectively define first and second exterior surface profiles that are inwardly facing relative to each other;
    the inlet oriented on a distal end of the first branch;
    the outlet oriented on a distal end of the second branch;
    the heat sink oriented between the first and second branches, with first and second opposed lateral surfaces, each of the respective first and second lateral surfaces defining respective first and second exterior surface profiles conforming respectively to the corresponding inwardly facing, exterior profiles of the first and second branches, in opposed, spaced orientation therewith;

the respective top and bottom surfaces of the heat sink each having a surface area of sixty to eighty five percent (60%-85%) of the corresponding surface area of its corresponding, respective upper and lower surfaces of the housing; and first and second solid, thermally conductive layers respectively interposed between and affixed to each of the respective corresponding first and second exterior surface profiles of the heat sink, and those of the first and second branches.

10. The cooling channel of claim 9, incorporated within a detector assembly, further comprising:

an electromagnetic radiation detector coupled to the lower surface of the housing;

a detector electronics package coupled to the upper surface of the housing; and an electrical connector, passing through the upper and lower surfaces of the housing, for communicating signals generated by the radiation detector to the detector electronics package.

11. The cooling channel of claim 9, further comprising:

a monolithic heat sink constructed of ceramic material;

the u-shaped cooling conduit constructed of metal;

each of the first and second conductive layers including a metallic layer deposited on its corresponding exterior surface profile of the heat sink, and a solder layer affixed to its corresponding metallic layer and to its corresponding exterior surface profile of the conduit branch; and the housing comprising a non-metallic molding that encapsulates the u-shaped cooling conduit and the heat sink therein.

12. The cooling channel of claim 11, incorporated within a detector assembly, further comprising:

an electromagnetic radiation detector coupled to the lower surface of the housing;

a detector electronics package coupled to the upper surface of the housing; and an electrical connector, passing through the upper and lower surfaces of the housing, for communicating signals generated by the radiation detector to the detector electronics package.

13. A medical imaging apparatus, comprising:

a gantry;

a coolant loop in the gantry, for absorption of heat generated within the gantry;

a gantry cooling apparatus coupled to the coolant loop, for receiving heat generated within the gantry;

coolant fluid circulating within the coolant loop;

a magnetic resonance imaging tube in the gantry, having therein:

at least one electromagnetic radiation detector and a detector electronics package coupled to the radiation detector, for receiving signals generated by the radiation detector, and;

a cooling channel in the gantry, having:

a non-metallic housing having a planar lower surface, coupled to the electromagnetic radiation detector, and a planar upper surface coupled to the detector electronics package;

a cooling conduit in the housing, having an exterior surface profile, an inlet and an outlet respectively coupled to the coolant loop for circulation of the coolant fluid therethrough;

a unitary, non-metallic heat sink in the housing, having respective continuous top and bottom surfaces in direct heat-conductive communication with the respective upper and lower surfaces of the housing, and a lateral surface between the top and bottom surfaces, the lateral surface having an exterior surface profile conforming to the exterior surface profile of the conduit, in opposed, spaced orientation with the conduit; and a solid, thermally conductive layer interposed between and affixed to the respective opposed, exterior surface profiles of the conduit and the heat sink.

14. The medical imaging apparatus of claim 13, the cooling channel further comprising:

the cooling conduit having a u-shaped planar profile, with first and second opposed branches joined at proximal ends thereof that respectively define first and second exterior surface profiles that are inwardly facing relative to each other;

the inlet oriented on a distal end of the first branch;

the outlet oriented on a distal end of the second branch;

the inlet and outlet respectively accessible outside the housing;

the heat sink oriented between the first and second branches, with first and second opposed lateral surfaces, each of the respective first and second lateral surfaces defining respective first and second exterior surface profiles conforming respectively to the corresponding inwardly facing, exterior profiles of the first and second branches, in opposed, spaced orientation therewith;

the respective top and bottom surfaces of the heat sink each having a surface area of sixty to eighty five percent (60%-85%) of the corresponding surface area of its corresponding, respective upper and lower surfaces of the housing; and first and second solid, thermally conductive layers respectively interposed between and affixed to each of the respective corresponding first and second exterior surface profiles of the heat sink, and those of the first and second branches.

15. The medical imaging apparatus of claim 14, the cooling channel further comprising:

a monolithic heat sink constructed of ceramic material;

the u-shaped cooling conduit constructed of metal;

each of the first and second conductive layers including a metallic layer deposited on its corresponding exterior surface profile of the heat sink, and a solder layer affixed to its corresponding metallic layer and to its corresponding exterior surface profile of the conduit branch;

a molded housing that encapsulates the u-shaped cooling conduit and the heat sink therein; and an electrical connector, passing through the upper and lower planar surfaces of the housing for communicating signals generated by the radiation detector to the detector electronics package.

16. The medical imaging apparatus of claim 15, further comprising fasteners accessible outside the housing that are embedded in the molding between the upper and lower planar surfaces of the housing, for coupling the housing, to the gantry.

17. A method for making a cooling channel for a gantry of a diagnostic medical imaging apparatus, comprising:
fabricating a cooling conduit, for circulation of coolant fluid therethrough, the conduit having an inlet, an outlet, and an exterior surface having a surface profile;
fabricating a unitary, non-metallic heat sink, having:
respective continuous top and bottom surfaces, and a lateral surface between the top and bottom surfaces, having an exterior surface profile conforming to the exterior surface profile of the conduit;
orienting the exterior surface profile of the conduit and the corresponding portion of the exterior surface profile of the heat sink, in opposed, spaced orientation therebetween;
rigidly coupling the conduit and the heat sink to each other by interposing and affixing a solid, thermally conductive layer to their respective corresponding, opposed and spaced exterior surfaces; and
enveloping the coupled conduit and heat sink within a non-metallic housing having respective upper and lower surface in direct heat-conductive communication with the respective top and bottom surfaces of the heat sink, with the inlet and an outlet of the conduit accessible outside the housing.

18. The method for making a cooling channel of claim 17, further comprising:
fabricating the heatsink as a monolithic block of ceramic material;
constructing the cooling conduit from metal;
rigidly coupling the conduit and the heatsink by depositing a metallic layer on the portion of the exterior surface of the ceramic heatsink that is coupled to the corresponding exterior surface profile of the conduit and soldering the metallic layer previously deposited on the ceramic heatsink to the corresponding exterior surface profile of the conduit; and
enveloping the coupled conduit by placing them in a mold and encapsulating them by filling the mold with non-solid, non-metallic material and hardening the non-metallic material to form a rigid housing.

19. The method for making a cooling channel of claim 18, further comprising:
fabricating the cooling conduit with a u-shaped planar profile, with first and second opposed branches joined at proximal ends thereof that respectively define first and second exterior surface profiles that are inwardly facing and laterally spaced relative to each other;
orienting the inlet on a distal end of the first branch;
orienting the outlet on a distal end of the second branch;
fabricating the ceramic heat sink with first and second opposed lateral surfaces, each of the respective first and second lateral surfaces defining respective first and second exterior surface profiles conforming respectively to the corresponding inwardly facing, exterior profiles of the first and second branches;
inserting the heat sink between the first and second branches, so that its respective first and second exterior surface profiles are in opposed, spaced orientation with the respective corresponding, inwardly facing, exterior profiles of the first and second branches; and
rigidly coupling the first and second branches to each of their corresponding first and second exterior surface profiles of the heat sink, by depositing respective metallic layers and soldering them to the corresponding exterior profiles of the first and second branches.

20. A method for fabricating a detector assembly for a gantry of a diagnostic medical imaging apparatus, incorporating the cooling channel made by the method of claim 19, comprising:
forming a through passage in the housing between its respective upper and lower planar surfaces, before or after hardening the polymer material;
inserting an electrical connector into the through passage,
coupling an electromagnetic radiation detector to the electrical connector and to the hardened, lower surface of the housing; and
coupling a detector electronics package to the electrical connector and to the upper surface of the housing, so that the detector electronics package can receive signals generated by the radiation detector.

* * * * *